(12) United States Patent
Kempner et al.

(10) Patent No.: US 12,236,583 B2
(45) Date of Patent: Feb. 25, 2025

(54) THREE-DIMENSIONAL LUMINESCENCE IMAGING

(71) Applicant: PerkinElmer Health Sciences, Inc., Waltham, MA (US)

(72) Inventors: Joshua Kempner, Medway, MA (US); Jorge Ripoll, Madrid (ES)

(73) Assignee: Revvity Health Sciences, Inc., Waltham, MA (US)

( * ) Notice: Subject to any disclaimer, the term of this patent is extended or adjusted under 35 U.S.C. 154(b) by 616 days.

(21) Appl. No.: 17/534,250

(22) Filed: Nov. 23, 2021

(65) Prior Publication Data
US 2023/0162349 A1 May 25, 2023

(51) Int. Cl.
*G06T 7/00* (2017.01)
*G06T 7/11* (2017.01)
*G06T 7/62* (2017.01)
*G06T 7/70* (2017.01)

(52) U.S. Cl.
CPC .............. *G06T 7/0012* (2013.01); *G06T 7/11* (2017.01); *G06T 7/62* (2017.01); *G06T 7/70* (2017.01)

(58) Field of Classification Search
CPC . G06T 7/0012; G06T 7/62; G06T 7/11; G06T 7/70
See application file for complete search history.

(56) References Cited

U.S. PATENT DOCUMENTS

| | | | |
|---|---|---|---|
| 2006/0045371 A1* | 3/2006 | Li | G06T 5/70 382/254 |
| 2006/0058683 A1* | 3/2006 | Chance | A61B 5/6834 600/407 |
| 2010/0097459 A1* | 4/2010 | Tholl | G01S 17/89 348/E5.022 |
| 2019/0138813 A1* | 5/2019 | Pereira | G06V 20/41 |
| 2020/0008899 A1* | 1/2020 | Tripathi | G02B 21/22 |
| 2020/0320775 A1* | 10/2020 | Holladay | G06T 7/11 |
| 2020/0321102 A1* | 10/2020 | Barnes | G06V 20/695 |
| 2020/0342597 A1* | 10/2020 | Chukka | G06V 20/698 |

(Continued)

OTHER PUBLICATIONS

Jianghong Zhong, Chenghu Qin, Xin Yang, Shuping Zhu, Xing Zhang, and Jie Tian, Cerenkov Luminescence Tomography for In Vivo Radiopharmaceutical Imaging, 2010 (Year: 2010).*

(Continued)

*Primary Examiner* — Kevin Ky
(74) *Attorney, Agent, or Firm* — Banner & Witcoff, Ltd.

(57) ABSTRACT

Systems, apparatuses, and methods are described for 3D luminescence imaging, by identifying a preferred optical pair and optimizing a scanned image using the preferred optical pair. An optimal filter pair may be selected from a list of two or more optical filters. An acceptable threshold of information may be obtained using a subset of the list of two or more optical filters (e.g., an optimal filter pair). An imaging device may be configured with the optimal filter pair to produce a pair of luminescence images of a target sample. In addition, luminescence images may be preprocessed to reduce the time-cost of conventional processing techniques of luminescence images. One or more computing devices may generate initial prior data based on a pair of luminescence images. An output may include one or more output luminescent sources that have been refined and/or optimized from the initial prior data.

20 Claims, 9 Drawing Sheets

(56) References Cited

U.S. PATENT DOCUMENTS

| | | | | |
|---|---|---|---|---|
| 2021/0027462 A1* | 1/2021 | Bredno | ............... | G06T 7/0012 |
| 2021/0295507 A1* | 9/2021 | Nie | ............... | G06T 7/0012 |
| 2022/0048256 A1* | 2/2022 | Michalica | ............ | G03F 7/70416 |
| 2022/0254094 A1* | 8/2022 | Wahrenberg | ........... | G06T 7/0012 |
| 2022/0301224 A1* | 9/2022 | Zhang | ............... | G06T 7/174 |
| 2024/0198209 A1* | 6/2024 | Hong | ............... | A63F 13/46 |
| 2024/0311994 A1* | 9/2024 | Ikeda | ............... | G01N 23/18 |

OTHER PUBLICATIONS

Kuo, Chaincy, Coquoz, Olivier, Troy, Tamara L., Xu, Heng, and Rice, Brad W., "Three-dimensional reconstruction of in vivo bioluminescent sources based on multispectral imaging," Journal of Biomedical Optics, vol. 12 (2), Mar./Apr. 2007, 12 pages.

"Pre-clinical in vivo imaging" Technical Note, Setup and Sequence Acquisition, PerkinElmer, (2012), 3 pages.

Caliper LifeSciences Living Image Software User's Manual, Version 3.2, 2002-2009, 276 pages.

Feb. 24, 2023—(WO) International Search Report and Written Opinion—App PCT/US2022/050540.

Zhong, Jianghong, et al., "Cerenkov Luminescence Tomography for In Vivo Radiopharmaceutical Imaging," International Journal of Biomedical Imaging, vol. 2011, Article ID 641618, 6 pages.

Zhong, Jianhong et al., "Robust image modeling technique with a bioluminescence image segmentation application," Proceedings of SPIE Smart Structures and Materials + Nondestructive Evaluation and Health Monitoring, 2005, San Diego, CA, vol. 7262, Feb. 26, 2009, downloaded from https:/www.spiedigitallibrary.org/conference-proceddings-of-spe on Feb. 15, 2023, 11 pages.

Feng, Jinchai, et al., "An optimal permissible source region strategy for multispectral bioluminescence tomography," Optics Express, vol. 16, No. 20, Sep. 29, 2008, 15 pages.

\* cited by examiner

THREE-DIMENSIONAL LUMINESCENCE IMAGING

FIELD OF USE

Aspects of the disclosure relate generally to luminescence imaging techniques and more specifically to identifying preferred relationships between pairs of optical filters and one or more luminescent sources.

BACKGROUND

Three-dimensional ("3D") luminescence imaging of a target sample may rely on low-throughput and time-costly conventional processing methods that require three or more optical filters. Moreover, these conventional processing methods may result in sub-optimal reconstructed sources, and require extended periods of time to process, on the order of 20-30 minutes per sample, overly limiting the number of samples that can be imaged in a finite amount of time.

SUMMARY

Systems, apparatuses, and methods are described for luminescence imaging, such as 3D bioluminescence imaging. The following presents a simplified summary of various aspects described herein. This summary is not an extensive overview, and is not intended to identify key or critical elements or to delineate the scope of the claims. The following summary merely presents some concepts in a simplified form as an introductory prelude to the more detailed description provided below. Corresponding apparatus, systems, and computer-readable media are also within the scope of the disclosure.

According to one aspect, the disclosure relates to a method for 3D luminescence imaging. The method may include receiving, by a computing device, a list of optical filters and data indicating a luminescent source and a scattering medium, such as a biological material. Filtered signals may be generated based on the list of optical filters and data received, and weights associated with one or more optical filter pairs may be determined. Each of the one or more optical filter pairs may be a pair of optical filters of the list of optical filters. The list of the one or more optical filter pairs may be ranked based on weights. A user device may be configured to receive filtered signals via the highest ranked optical filter pair of the ranked list.

In some implementations, each of the weights may correspond to a numerical value, and a highest ranked optical filter pair may correspond to a largest numerical value of the weights. An optical filter pair may include a first optical filter and a second optical filter. A weight associated with the optical filter pair may be determined, in part, by determining a correlation between the first and second optical filters, such as between a first filtered signal of the filtered signals associated with the first optical filter and a second filtered signal of the filtered signals associated with the second optical filter. In some implementations, the weight may be determined, in part, by determining a ratio of the first filtered signal and the second filtered signal. In some implementations, the weight may be determined, in part, by comparing each of the first filtered signal and the second filtered signal with a pre-determined threshold value. In some implementations, the weight may be determined, in part, by determining a product of the first filtered signal and the second filtered signal. In some implementations, determining a weight associated with an optical filter pair may include determining a linear relationship between the first filtered signal and the second filtered signal. In some implementations, determining a weight associated with an optical filter pair may include determining a rank of a matrix that has at least a first column including the first filtered signal and a second column including the second signal.

In some implementations, generating the filtered signals may include computing filtered signals for a plurality of distances. Each of the plurality of distances may correspond to a distance between a portion of the luminescent source and a surface boundary of the scattering medium. In some implementations, generating a filtered signal may be based on a source model. In some implementations, generating the filtered signals may include generating a volume of the biological material. The volume may include one or more voxels, each of which may be assigned a numerical value corresponding to a radiated intensity of the luminescent source.

In some implementations, the computing device may receive data indicating a second luminescent source and a second biological material. Additional filtered signals may be generated based on the list of optical filters, the second luminescent source, and the second biological material. Additional weights, associated with the one or more optical filter pairs, may be determined based on the additional filtered signals. The second list of the one or more optical filters may be ranked based on the additional weights. A highest ranked optical filter pair may be selected from the ranked second list of the one or more optical filter pairs.

According to still another aspect of the present disclosure, an optical filter pair for imaging a luminescent source in a volume of biological material is provided. The optical filter pair may be selected from a list of available optical filters according to any of the methods disclosed herein.

Another aspect of the present disclosure is a method of optimizing a scanned image. The method may include receiving, from a user device, one or more images associated with one or more optical filters and a bioluminescent source located within a volume of biological material. An image dataset may be generated based on the one or more images and one or more image segments may be determined based on the image dataset. One or more volume sub-regions associated with the one or more image segments may be generated. Each of the one or more volume sub-regions may include voxels, each of which may be assigned one or more radiation values determined based on the bioluminescent source, the volume of biological material, and the one or more optical filters. An output volume including output voxels may be determined based on the one or more volume sub-regions. The one or more output radiation values may be assigned to each of the output voxels. The output volume region may be sent to a computing device for additional processing. In some implementations, the output volume region may be sent to a storage device. In some implementations, the one or more optical filters include a first optical filter and a second optical filter, and correspond to an optical filter pair.

In some implementations, the image dataset may include a plurality of pixels, and the one or more image segments of the image dataset may be determined by comparing numerical values of the pixels with a threshold value. In some implementations, a quantity of the one or more image segments may be less than a pre-determined quantity of image segments. In some implementations, a distance between a voxel associated with the volume sub-region and a surface boundary of the volume of biological material may be determined for a volume sub-region. In some implementations, the output volume region may be determined based on performing an average, for one or more voxels of the one or more volume sub-regions, of the radiation values assigned to the one or more voxels. In some implementations, the user device is a three-dimensional bioluminescence imaging device.

In some implementations, an image segment may correspond to a volume sub-region determined by generating one or more volume test-regions, each of which includes one or more voxels assigned one or more radiation test-values. The one or more radiation test-values may be determined based on the bioluminescent source, the biological material, and the one or more optical filters. One or more test images may be generated based on the one or more radiation test-values, assigned to the one or more voxels, and the one or more optical filters. Image test segments may be generated based on the one or more test images. A correlation between the image test-segment and the image segment may be determined for each image test segment, and a volume test region may be selected as the volume sub-region based on determining a highest correlation value of an image test-segment.

In some implementations, one or more additional images may be received from a user device, the one or more additional images being associated with one or more additional optical filters and the bioluminescent source located within the volume of biological material. A second image dataset may be generated based on the one or more additional images and one or more additional image segments may be determined based on the second image dataset. One or more additional volume sub-regions associated with the one or more additional image segments may be generated. Each of the one or more additional volume sub-regions may include voxels, each of which may be assigned one or more radiation values determined based on the bioluminescent source, the volume of biological material, and the one or more additional optical filters. A second output volume region including additional output voxels may be generated based on the one or more additional volume sub-regions. One or more output radiation values may be assigned to each of the additional output voxels. The second output volume region may be sent to the computing device for additional processing.

According to another aspect of the present disclosure, one or more non-transitory computer-readable media are provided that store instructions that, when executed, cause one or more of the methods disclosed herein to be performed. According to another aspect of the present disclosure, a system including one or more processors and memory storing instructions that, when executed by the one or more processors, cause the system to perform one or more of the methods disclosed herein.

Additional aspects, configurations, embodiments and examples are described in more detail below.

BRIEF DESCRIPTION OF THE DRAWINGS

Some features are shown by way of example, and not by limitation, in the accompanying drawings. In the drawings, like numerals reference similar elements.

DETAILED DESCRIPTION

Figure 1:
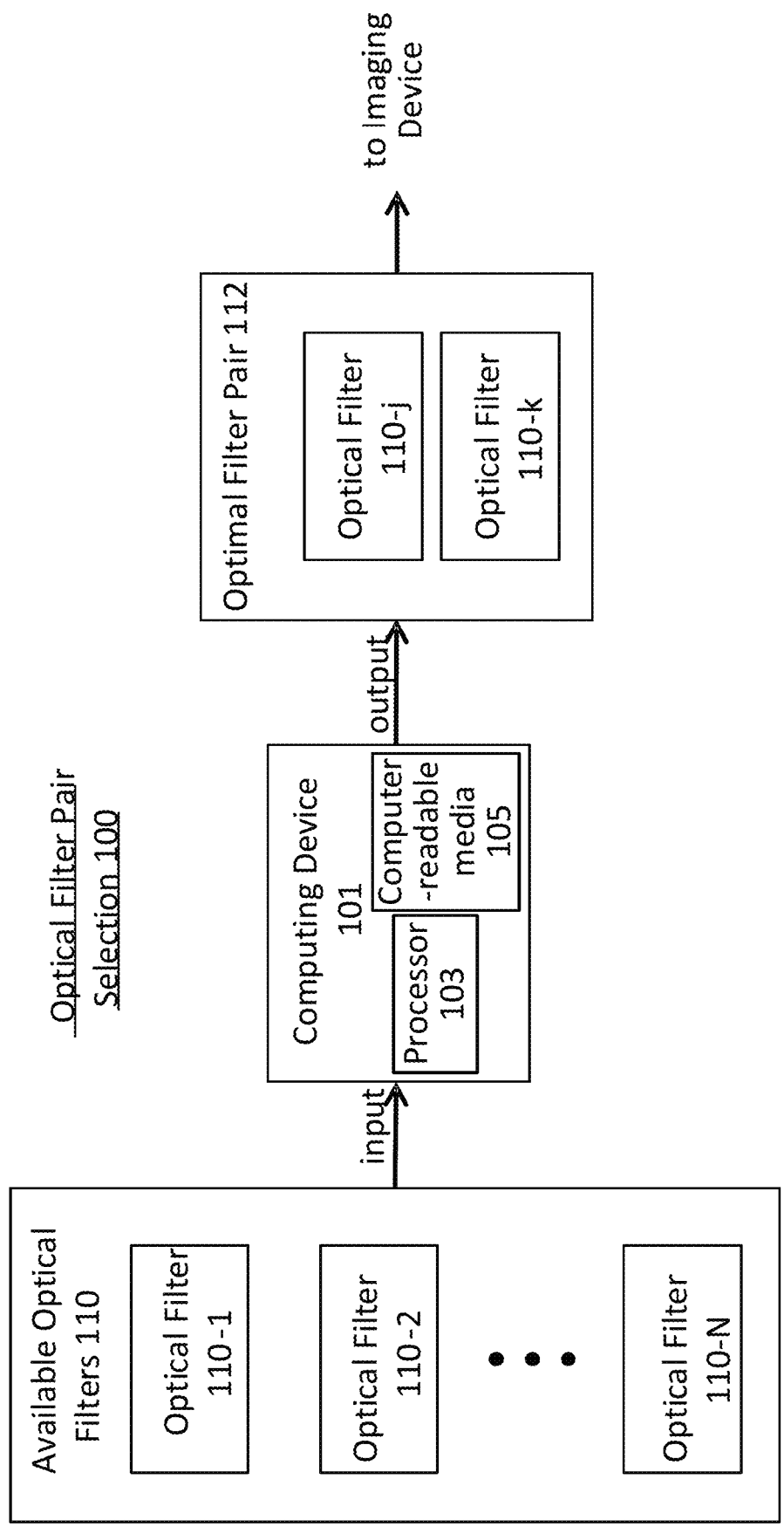
FIG. 1 shows an example optical filter pair selection process.

The inventors have recognized and appreciated that luminescence imaging, such as bioluminescence imaging and chemiluminescence imaging, can be time consuming and slow, resulting in low throughput when processing samples. In particular, 3D luminescence imaging may require taking multiple images using multiple filters, typically three or more, and more typically six or more. At the same time, luminescence imaging can be time sensitive due to, for example, time constrictions of anesthesia in the case of biological samples and luminescence source kinetics. As such, scientists and laboratory technicians often select other methods for achieving their various end goals. Consequently, aspects describes herein provide new methods and systems that reduce the amount of time needed to perform luminescence imaging without substantially compromising accuracy or quality, thereby creating a path forward for an increase of use of luminescence imaging for a wider range of applications.

In some embodiments, a number of optical filters used to perform luminescence imaging can be reduced from three or more to only two optical filters without substantial loss of image and measurement accuracy or quality. The reduction in the number of filters used to acquire image data reduces the data acquisition time needed. For example, if data acquisition with a single optical filter takes 2-5 minutes, then conventionally acquiring data using six optical filters takes on the order of 30 minutes. On the other hand, in some embodiments, using only two optical filters can shorten the time for data acquisition down to 5-10 minutes. Using two optical filters that provide complementary information with sufficient signal to noise ratios may allow for shortened time for data acquisition without loss of image and measurement accuracy or quality.

In some embodiments, the number of optical filters used can be reduced to a single pair of filters by determining an optimal filter pair, to use for a particular purpose, from a list of available optical filters. The optimal filter pair may be determined without first performing any luminescence imaging or any physical optimization of a filter pair on a sample to be imaged. An optimal filter pair may be selected from a list of two or more optical filters. For example, one or more computing devices may determine, based on performing one or more electromagnetic simulations, that one or more optical filters of the list of optical filters may be discarded without reducing the amount of measured spectral information of a luminescent source below an acceptable threshold of information. The acceptable threshold of information may be obtained using a subset of the list of two or more optical filters (e.g., an optimal filter pair). An imaging device may be configured with the optimal filter pair to produce a pair of luminescence images of a target sample.

The inventors have also recognized and appreciated that image reconstruction from the acquired luminescence imaging data is a time consuming, iterative process. Conventional image reconstruction techniques use an "unintelligent" initial guess as initial prior data to initiate the reconstruction process. The inventors have also recognized and appreciated that using a fast, simple estimation process to generate initial prior data can significantly increase the speed of conventional reconstruction techniques because a small number of iterations is needed to generate the final image reconstruction. Thus, in some embodiments, image reconstruction is performed using a two-phase reconstruction, unlike the single-phase reconstruction of conventional methods. In the two-phase reconstruction, some embodiments perform pre-processing, which may include making a rough estimate of one or more luminescent sources, during the first phase. For example, one or more computing devices may generate initial prior data based on a pair of luminescence images. The initial prior data may include data indicating one or more luminescent sources. This rough estimate of the one or more luminescent sources may then be used as initial prior data in a more conventional image reconstruction technique. An output of the image reconstruction technique may be one or more output luminescent sources that have been refined and/or optimized from the initial prior data. These and other features and advantages are described in greater detail below.

FIG. 1 shows an example method 100 for selecting an optical filter pair from a list of available optical filters 110. For example, a computing device 101 may determine an optimal filter pair by performing methods discussed below in connection with FIGS. 2A-2C. The optimal filter pair may be used for imaging a target sample in a luminescence imaging system.

The computing device 101 may comprise one or more processors 103, which may execute instructions of a computer program to perform any of the functions described herein. The instructions may be stored in one or more non-transitory computer-readable media 105 (e.g., a random access memory (RAM)). The computing device 101 may further comprise one or more data interfaces (a USB port, a CD/DVD drive, one or more network ports, a modem, etc.), one or more output devices (e.g., a display device, a speaker, etc.), and/or one or more user input devices (e.g., a keyboard, a mouse, a touch screen, microphone, etc.).

The list of available optical filters 110 may comprise optical filters capable of spectrally filtering light. For example, the list of available optical filters 110 may comprise at least one or more of an absorptive optical filter, a dichroic optical filter, a monochromatic optical filter, an infrared filter, an ultraviolet filter, an interference filter, a thin-film filter, a long-pass optical filter, a band-pass optical filter, a short-pass optical filter or a machine vision filter. Moreover, the list of available optical filters 110 may comprise optical filters comprising optical materials such as optical glass (e.g., $CaF_2$, Fused Silica, S-$FSL_5$, N-$BK_7$, other types of optical glass) and/or absorptive coatings (e.g., anti-reflective coatings, dielectric mirror coatings, short-wave pass filter coatings, longwave pass filter coatings, bandpass filter coatings, dichroic filter coatings, notch filter coatings, etc.). Furthermore, the optical filters may correspond to a geometric shape such as a circle, a cylindrical disk, a square, a rectangular prism, or any other 2- or 3-dimensional shape.

The computing device 101 may receive optical filter data comprising the list of available optical filters 110 and additional data via one or more of its data interfaces. For example, the optical filter data and additional data may be received via keyboard input, a CD-ROM, a USB flash drive, or any other device suitable for transferring data. As discussed below in connection with FIGS. 2A-2C, the computing device 101 may determine, from the optical filter data, an optical filter pair such as the optimal filter pair 112 depicted in FIG. 1. The optimal filter pair 112 may comprise a pair of optical filters (e.g., optical filter 110-$j$ and optical filter 110-$k$ shown in FIG. 1) selected by the computing device 101 from the list of available optical filters 110. A pair of optical filters (e.g., optical filter 110-$j$ and optical filter 110-$k$ shown in FIG. 1) may be selected to be an optimal filter pair 112 based on a ranked list of pairs of optical filters chosen from the list of available optical filters 110. The optimal filter pair may be the highest ranked pair of optical filters of the ranked list. The selected optimal filter pair 112 may be sent to an output device of the computing device 101. For example, information indicating the selected optimal filter pair 112 may be displayed on a computer monitor. Also or alternatively, information indicating the selected optimal filter pair 112 may be stored, for access by one or more users, on a storage device associated with the computing device 101 (e.g., a USB flash drive, a hard drive, etc.). Furthermore, a luminescence imaging device (not shown) may be configured to image one or more targets (e.g., a tissue sample, small animals, rodents, other biological material, etc.) using the optimal filter pair 112. For example, a luminescence imaging device may be configured with the optimal filter pair 112 to produce a luminescence image pair (e.g., a luminescence image generated for each optical filter of the optimal filter pair 112). As is discussed below in connection with FIG. 3 and FIGS. 4A-4C, a computing device (e.g., computing device 101 or another computing device) may perform pre-processing of the luminescence images and generate initial prior data as input for additional image processing.

Figure 2A:
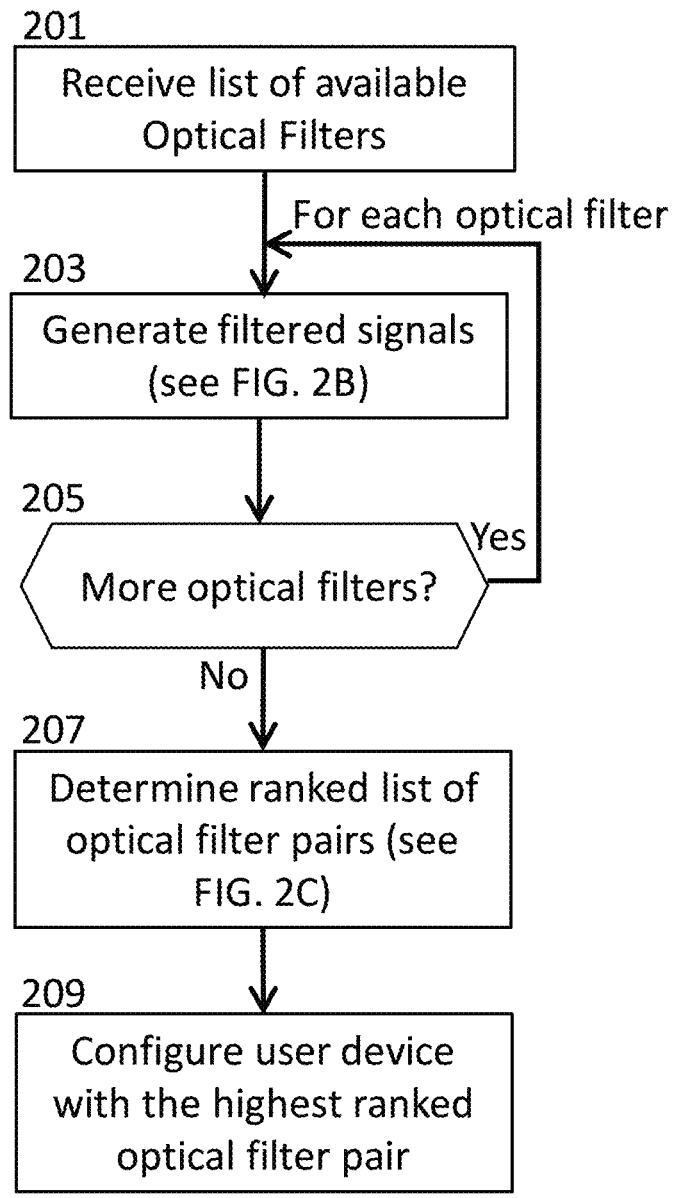
FIGS. 2A, 2B, and 2C are a flowchart showing an example method of determining an optical filter pair.
Figure 2B:
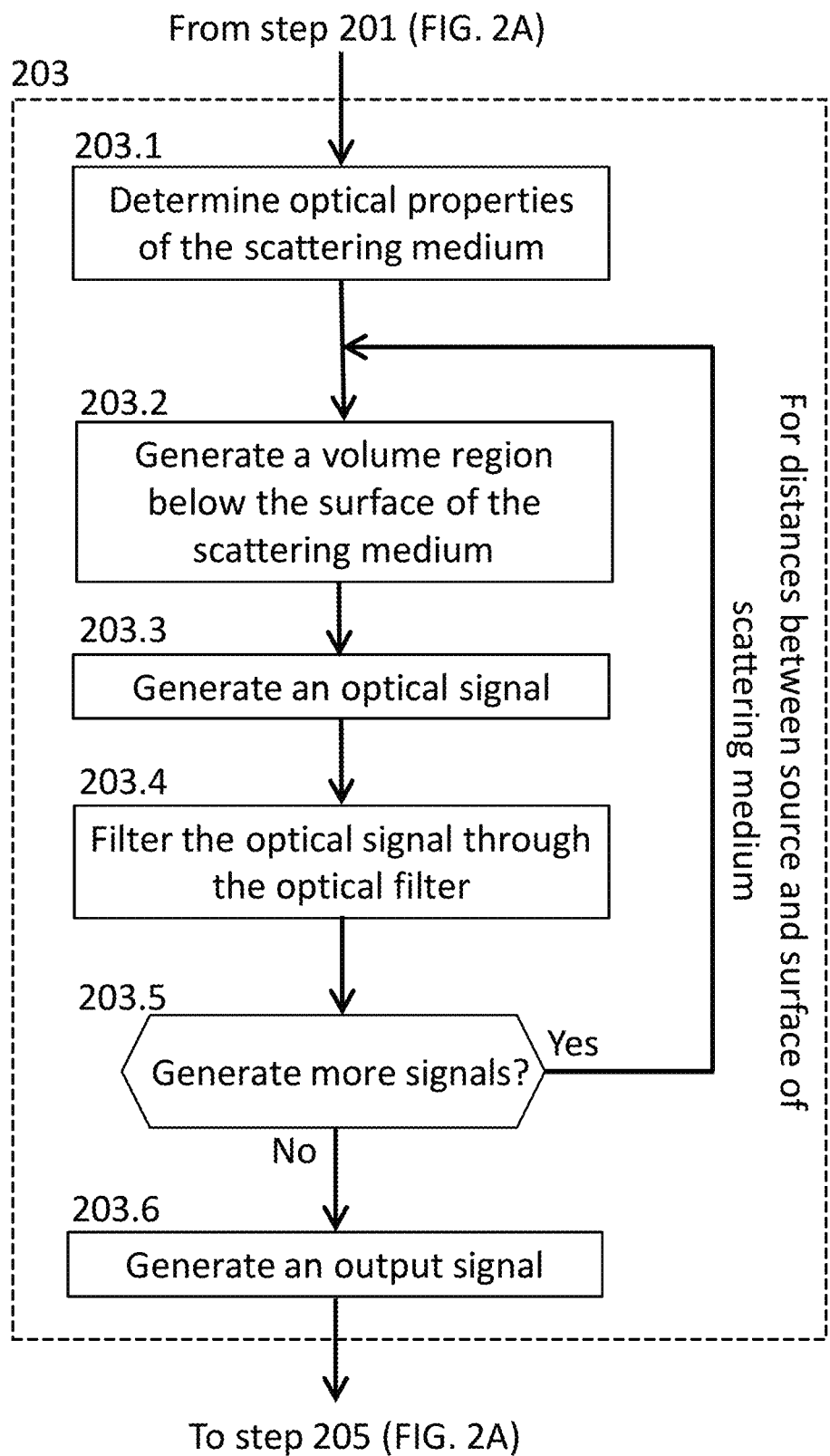
Figure 2C:
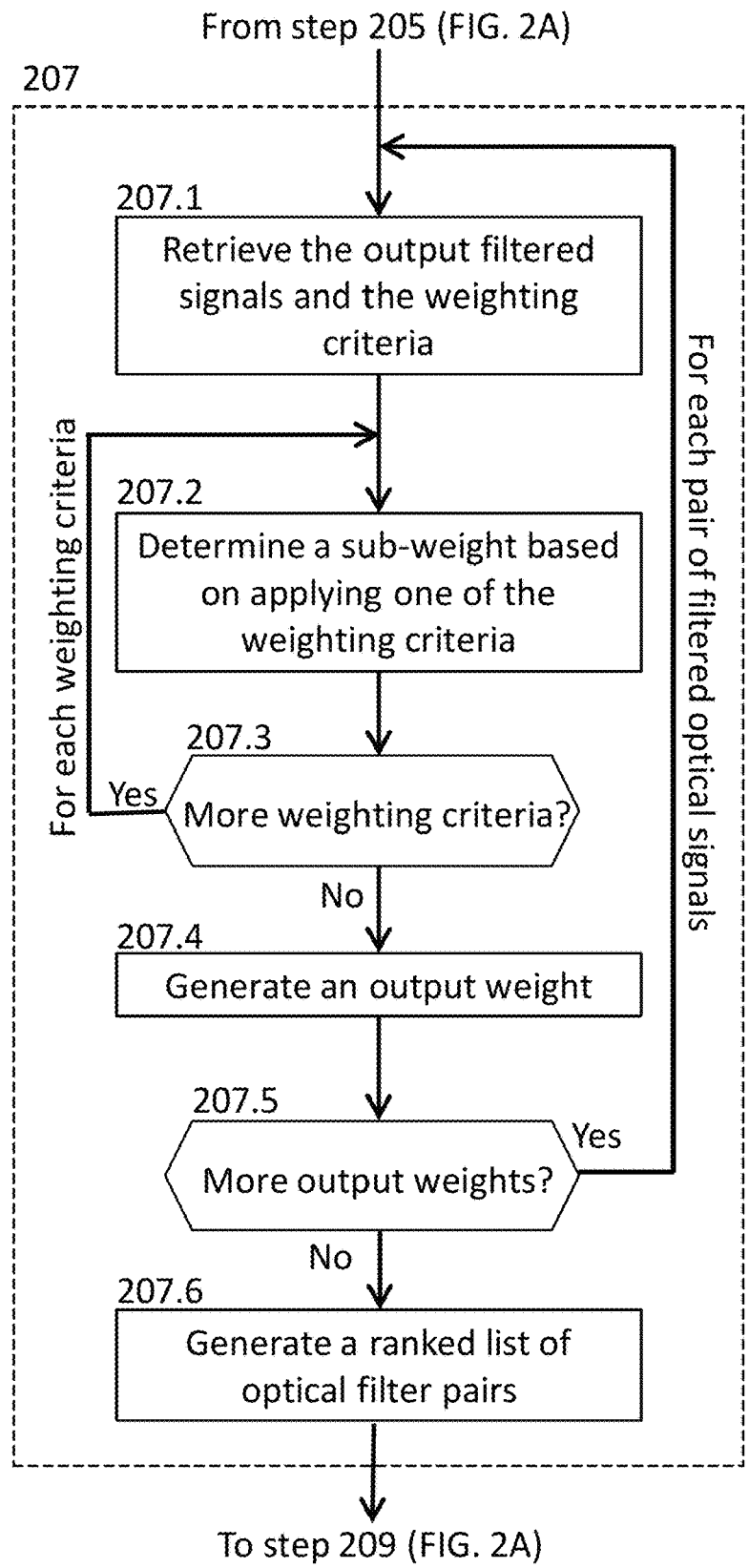

FIGS. 2A-2C are a flowchart showing an example method of determining an optimal filter pair. One, some, or all steps of the example method of FIGS. 2A-2C may be performed by the computing device 101, and for convenience FIGS. 2A-2C will be described below in connection with the computing device 101. Also or alternatively, one, some, or all steps of the example method of FIGS. 2A-2C may be performed by one or more other computing devices. One or more steps of the example method of FIGS. 2A-2C may be rearranged (e.g., performed in a different order), omitted, and/or otherwise modified, and/or other steps added.

In step 201, optical filter data comprising a list of available optical filters (e.g., the list of available optical filters 110) may be received (e.g., by the computing device 101). Furthermore, additional data may be received, the additional data comprising additional information associated with the list of available optical filters, a luminescent source and/or scattering media. For example, the additional information may indicate a type of the luminescent source for use with an optimal filter pair (e.g., a bioluminescent source such as firefly luciferase, renilla luciferase, bacterial luciferase, dinoflagellate luciferase, Metridia luciferase, or any other source of luminescent light). Moreover, the additional information may comprise radiation characteristics of the luminescent source (e.g., power spectral density, kinetic spectral light emission profile, or other spectral features of the emitted radiation of the source) and characteristics for each of the optical filters of the list of optical filters (e.g., optical filter type, spectral characteristics, etc.). The additional information may further comprise optical characteristics (e.g., permittivity, dielectric constant, refractive index, etc.) of a scattering medium (e.g., biological material). The computing device 101 may be configured to proceed to step 203 upon receiving the list of available optical filters. Alternatively, the computing device 101 may be configured to await instructions (e.g., instructions received via user input) prior to proceeding to step 203.

In step 203, an optical filter may be selected from the list of available optical filters 110. A filtered signal may be generated (e.g., by the computing device 101) based on the selected optical filter and the additional information received in step 201. For example, the computing device 101 may generate a filtered signal based on the selected optical filter, a luminescent source, and a scattering medium. The filtered signal may be generated, via one or more electromagnetic signal propagation models and/or one or more signal processing techniques, based on an optical signal emitted from the luminescent source, scattered and/or attenuated in the scattering medium, and filtered by the selected optical filter. Moreover, spectral characteristics of the filtered signal may be sent to an output device (e.g., to a display device and/or a storage device) for retrieval and use in additional steps discussed below in connection with FIG. 1 and FIGS. 2A-2C. Additional details of step 203 are described below in connection with FIG. 2B.

In step 205, the computing device 101 may determine whether there are additional optical filters available for selection from the list of available optical filters 110. If the computing device 101 determines that there are additional optical filters for selection, the computing device 101 may select another optical filter for use in step 203 and step 203 may be performed. Otherwise, step 207 may be performed.

In step 207, a ranked list of optical filter pairs may be determined. For example, the computing device 101 may determine, for an optical filter pair comprising a pair of optical filters selected from the available list of optical filters 110, a ranking based on filtered signals generated, e.g., in step 203, for the two selected optical filters. The ranking may be a value assigned based on a weighting factor determined for the optical filter pair. For example, an optical filter pair with a high weighting factor may be assigned a high rank and another optical filter pair with a low weighting factor may be assigned a low rank. The weighting factor may be determined based on applying one or more weighting criteria to the filtered optical signals corresponding to the optical filter pair. Additional details of step 207 are described below in connection with FIG. 2C.

In step 209, a highest ranked optical filter pair may be selected from the ranked list of optical filter pairs. The highest ranked optical filter pair may be determined to be an optimal filter pair. An indication of the optimal filter pair may be sent to at least one of an output, display, and/or storage device (e.g., of the computing device 101). A user device (e.g., a luminescence imaging device) may be configured according to the optimal filter pair. For example, a user may configure the user device to image one or more targets based on the optimal filter pair.

FIG. 2B shows, as indicated by a broken line box, additional details of step 203 from FIG. 2A. In particular, FIG. 2B shows examples steps 203.1-203.6 that may be performed to generate filtered optical signals for each of the optical filters in the list of available optical filters 110. In step 203.1, a scattering medium may be generated based on the additional data received in step 201. For example, the additional data received in step 201 may comprise one or more optical properties of a tissue sample (e.g., tissue permittivity, tissue dielectric constant, tissue scattering and/or absorption properties). The one or more optical properties may be derivable via experimentally measured data. For example, the optical characteristics may comprise experimentally measured optical permittivity values for one or more spectral components associated with the optical filter pair. Also or alternatively, the one or more optical properties may be derivable via theoretical models. For example, the optical characteristics may comprise a damping factor and/or an electron relaxation time. The computing device 101 may, e.g., generate optical permittivity values for the scattering medium based on the damping factor and a permittivity model (e.g., a bound-electron oscillator model, the Debye relaxation model, etc.). The scattering medium may be generated to fill a volume bound by one or more surface boundaries.

In step 203.2, a volume region comprising a plurality of voxels within the scattering medium may be selected, e.g., by user input, or generated, e.g., via computer simulation. Each of the plurality of voxels may be assigned one or more radiation values corresponding to the luminescent source and the scattering medium. For example, the computing device 101 may assign a radiated intensity to a voxel with similar spectral characteristics as the luminescent source located within the scattering medium. A shape of the volume region may be spherical, ellipsoidal region, or any other contiguous region(s) of space.

A center of the volume region may be used to define a surface distance between the volume region and a surface boundary separating the scattering medium and a neighboring region having optical properties consistent with a different media, such as air or free-space. The center of the volume region may be a center of a spherical region, a center of symmetry of an ellipsoidal region, a center-of-mass, or any other portion of the volume region. A surface distance of the volume region may be a distance between the center of the volume region and a closest portion of the surface boundary of the scattering medium. A volume region near the surface boundary (e.g., a surface distance is below a pre-determined threshold value) may be generated, e.g., by the computing device 101, with an ellipsoidal shape. A volume region far from the surface boundary (e.g., a surface distance is above a threshold value) may be generated with a spherical shape. Also or alternatively, volume regions may be generated as any arbitrary shape at any surface distance. Moreover, the volume region of the luminescent source may be configured to emit optical radiation according to the radiation characteristics of the additional information received in step 201. For example, the volume region may comprise a plurality of voxels. Each voxel may be assigned a radiation value (e.g., radiated intensity, radiated electric field strength) based on the radiation characteristics received in the additional information.

In step 203.3, an optical signal comprising one or more spectral components associated with the optical filter pair may be generated using an electromagnetic model (e.g., a model derivable from Maxwell's equations) and/or one or more electromagnetic numerical solver techniques (e.g., finite-difference-time-domain, finite-element-method, method-of-moments, etc.). For example, the computing device 101 may simulate the emission of an optical signal from the luminescent source in the scattering medium. Moreover, the emitted optical signal may be attenuated and/or dispersed based on the optical characteristics (e.g., such as determined in step 203.1) of the scattering medium. The computing device 101 may simulate refraction (e.g., based on Snell's Law) of the optical signal at the surface boundary of the scattering medium.

In step 203.4, the optical signal may be filtered, after exiting the scattering medium via the surface boundary, by the selected optical filter. For example, the computing device 101 may simulate the propagation, of at least a portion of the refracted optical signal, through an optical filter. A filtered signal may be determined based on using signal processing techniques (e.g., a Fourier Transform, a convolution, etc.). The filtered signal may comprise numerical values for each of the one or more spectral components of the optical signal. For example, the numerical values may correspond to a received optical power (e.g., irradiance, flux density, optical power, and/or spectral irradiance).

In step 203.5, the computing device 101 may determine whether additional filtered optical signals should be generated using the selected optical filter. For example, the additional information received in step 201 may comprise an indication that filtered optical signals should be generated, for one or more surface distances between the volume region of the luminescent source and the surface boundary of the scattering medium. If the computing device 101 determines that additional optical signals should be generated using the selected optical filter, step 203.2 may be performed. Otherwise, if the computing device 101 determines that no additional optical signal should be generated using the selected optical filter, step 203.6 may be performed.

In step 203.6, an output filtered signal may be generated based on the filtered signals generated in steps 203.2-203.5. For example, the output filtered signal may be generated based on performing an average of the filtered signals. Also or alternatively, the output filtered signal may be generated based on performing a weighted sum of the filtered optical signals. For example, filtered optical signals generated for luminescent sources near the boundary surface of the scattering medium may be given higher weight than filtered optical signals generated for luminescent sources further from the boundary surface. Alternatively, filtered signals generated for luminescent sources far from the boundary surface of the scattering medium may be given higher weight than filtered optical signals generated for luminescent sources near the boundary surface. Alternatively, filtered signals generated for luminescent sources may be given equal weight independent of source distance from the boundary surface of the scattering medium. The output filtered signal for the selected optical filter may be sent to one or more of a display device, a storage device, or other output device of the computing device 101.

FIG. 2C shows, as indicated by a broken line box, additional details of step 207 from FIG. 2A. In particular, FIG. 2C shows examples steps 207.1-207.6 that may be performed to generate a ranked list of optical filter pairs based on the output filtered signals generated in step 203 for each of the optical filters. In step 207.1, one or more weighting criteria for the stored output filtered signals generated in step 203 may be retrieved (e.g., via the additional information received in step 201). The one or more weighting criteria may comprise one or more criteria for determining a performance relationship between two optical filters (i.e., an optical filter pair) from the list of available optical filters 110. For example, the one or more weighting criteria may be associated with determining a correlation between two optical filters of an optical filter pair. Also or alternatively, the one or more weighting criteria may be used to determine that the output filtered signals associated with the optical filter pair meet additional criteria such as satisfying minimum output filtered signal powers or minimum signal-to-noise ratio for each output filtered signal.

In step 207.2, the computing device 101 may determine, based on one of the one or more weighting criteria, a sub-weight for an optical filter pair (e.g., a pair of optical filters selected from the list of available optical filters 110). The sub-weight may be determined based on using the output filtered signals (e.g., power spectral density, spectral intensity, etc.) generated in step 203 as input to the weighting criteria. For example, the weighting criteria may comprise calculating a ratio of a sum of a first output filtered signal $I_1$ and a sum of a second output filtered signal $I_2$. The first output filtered signal $I_1$ may be associated with a first optical filter of the selected optical filter pair. The second output filtered signal $I_2$ may be associated with a second optical filter of the selected optical filter pair. The weighting criteria may be computationally represented as $w_{ratio}=\Sigma_i I_{1,i}/\Sigma_j I_{2,j}$, where the sums are performed over each spectral component of $I_1$ and $I_2$.

Also or alternatively, the weighting criteria may comprise determining a total number of values of the first and second output filtered signals that are above a threshold value. For example, the first output filtered signal $I_1$ may comprise $N_1$ spectral components where $N_1$ is an integer. The computing device 101 may determine that an integer number $n_1$ of the spectral components are above the threshold value, where $n_1 \leq N_1$. Similarly, the second output filtered signal $I_2$ may comprise $N_2$ spectral components where $N_2$ is an integer. The computing device 101 may determine that an integer number $n_2$ of the spectral components are above the threshold value, where $n_2 \leq N_2$. The weighting criteria may be computationally represented as $w_n=(n_1+n_2)/(N_1+N_2)$.

Also or alternatively, the weighting criteria may comprise determining a product of the first output filtered signal $I_1$ and the second output filtered signal $I_2$, or a normalized product. The weighting criteria may be computationally represented as $w_{product}=2\Sigma_i I_{1,i} \Sigma_j I_{2,j}/((\Sigma_i I_{1,i})^2+(\Sigma_j I_{1,j})^2)$, where the sums are performed over each spectral component of $I_1$ and $I_2$.

Also or alternatively, the weighting criteria may comprise determining a linear relationship between the first output filtered signal $I_1$ and the second output filtered signal $I_2$. For example, a numerical relationship f may be defined such that $I_2=f(I_1)$. A goodness-of-fit value R may be determined based on the numerical relationship f, where $0 \leq R \leq 1$. The goodness-of-fit value R may indicate correlation of the numerical relationship f with a linear function. The weighting criteria may be computationally represented as $w_R=1-R$.

Also or alternatively, the weighting criteria may comprise determining a rank of a matrix comprising the first output filtered signal $I_1$ in a first column and the second output filtered signal $I_2$ in a second column. For example, a rank of a matrix $M=[\vec{I}_1 \; \vec{I}_2]$ may be determined, where $\vec{I}_1$ and $\vec{I}_2$ are vectors corresponding to the first output filtered signal $I_1$ and the second output filtered signal $I_2$. The vector elements of the vectors $\vec{I}_1$ and $\vec{I}_2$ may correspond to the spectral component of $I_1$ and $I_2$, respectively. If $\vec{I}_1$ and $\vec{I}_2$ are linearly independent, then rank(M)=2. If $\vec{I}_1$ and $\vec{I}_2$ are linearly dependent, then rank(M)=1. Generally, a rank of the matrix M may be 1 or 2. The weighting criteria may be computationally represented as $w_{rank}=\text{rank}([\vec{I}_1, \vec{I}_2])-1$.

In step 207.3, the computing device may determine whether to apply additional weighting criteria to the first and second output filtered signals. If a determination is made to apply additional weighting criteria, step 207.2 may be performed. Otherwise step 207.4 may be performed.

In step 207.4, an output weight for the selected optical filter pair may be generated based on one or more sub-weights calculated in step 207.2. For example, the computing device 101 may calculate an output weight by taking a product of the one or more sub-weights (e.g., $w_{final}=w_{ratio} \times w_n \times w_{product} \times w_R \times w_{rank}$). Alternatively, the computing device 101 may calculate an output weight be taking a weighted sum of the one or more sub-weights. For example, the output weight may be computationally represented as $w_{final}=\rho_{ratio}w_{ratio}+\rho_n w_n+\rho_{product}w_{product}+\rho_R w_R+\rho_{rank}w_{rank}$, where the weighting factors are real numbers and obey the relationship $\rho_{ratio}+\rho_n+\rho_{product}+\rho_R+\rho_{rank}=1$). Alternatively, the computing device 101 may calculate an output weight based on using the sub-weights as inputs to any other algorithm and/or mathematical relationship indicated by the additional information received in step 201.

In step 207.5, the computing device 101 may determine whether to calculate an output weight for an additional optical filter pair. The information received in step 201 may comprise instructions to calculate an output weight for every possible pairing of optical filters in the list of available optical filters 110. For example, the computing device 101 may determine, from the list of available optical filters 110, a list of optical filter pairs comprising every possible pairing of optical filters. The computing device 101 may calculate an output weight for each optical filter pair from the list of optical filter pairs. If a determination is made to calculate an output weight for an additional optical filter pair, step 207.1 may be performed. Otherwise step 207.6 may be performed.

In step 207.6, a ranked list of optical filter pairs may be generated. For example, the computing device may sort the list of optical filter pairs based on the output weights. A high output weight value may correspond to a high ranked optical filter pair and a low output weight value may correspond to a low ranked optical filter pair.

Figure 3:
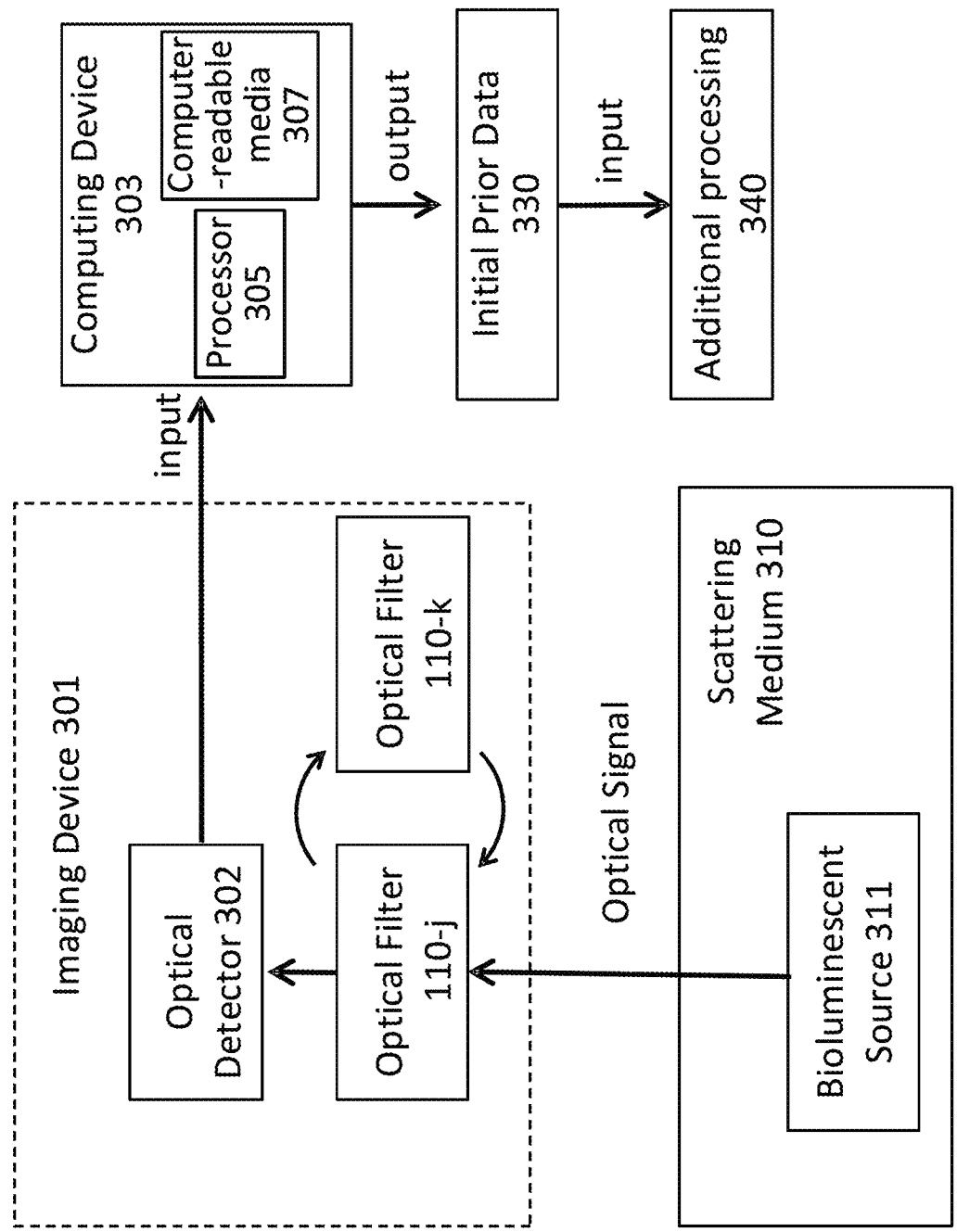
FIG. 3 shows example 3D luminescence imaging process.

FIG. 3 shows an example 3D luminescence imaging process. An imaging device 301 (e.g., an IVIS Spectrum series imaging device or any other 3D luminescence imaging device) may be configured with an optimal filter pair (e.g., optical filters 110-$j$ and 110-$k$ shown in FIG. 3) and an optical detector 302. The optical filter pair may correspond to a highest ranked optical filter pair selected from a ranked list of optical filter pairs (e.g., such as the ranked list of optical filter pairs determined based on performing steps 201-209 of FIG. 2A). The optical detector 302 may receive an optical signal that has been filtered through one of the optical filters of the optimal filter pair.

For example, the imaging device 301 may be configured to produce images based on optical signals emitted by a luminescent source 311. The luminescent source 311 may emit an optical signal (e.g., visible light corresponding to wavelengths between 400 to 700 nm) within a scattering medium 310 (e.g., a biological tissue sample). The emitted optical signal may propagate through the scattering medium, exit the scattering medium, and pass through and be filtered through a first optical filter (e.g., optical filter 110-$j$ or 110-$k$). The filtered optical signal may be received by an optical detector 302 and used, by the imaging device 301, to generate a first image.

After generating a first image based on the first optical filter, the imaging device 301 may also be configured to image the luminescent source 311 based on a second optical filter (e.g., whichever of optical filter 110-$k$ or 110-$j$ was not used to produce the initial image). The luminescent source 311 may emit another optical signal, which may propagate through the scattering medium, exit the scattering medium, and pass through the second optical filter. Upon exiting the second optical filter, the filtered optical radiation may be received by the optical detector and used, by the imaging device 301, to generate a second image.

After imaging the luminescent source 311 based on the first and second optical filters, the imaging device 301 may output the first image based on the first optical filter (e.g., optical filter 110-$j$) and the second image based on the second optical filter (e.g., optical filter 110-$k$). The first and second images may be input into a computing device (e.g., the imaging device 301, computing device 101, or computing device 303), for image pre-processing and the generation of initial prior data 330 (e.g., an initial source estimation that may be used as an input to a conventional luminescence image processing method). For example, and as discussed below in connection with FIGS. 5A-5C, the computing device 303 may, upon receiving the first and second images, generate an initial representation of the luminescent source 311. The initial representation of the luminescent source 311 may correspond to a first "pass" computational reconstruction of the luminescent source 311, and may serve as an initial input to subsequent conventional reconstruction techniques. For example, the initial representation of the luminescent source 311 may comprise, for one or more volume regions of the scattering medium 310, one or more luminescent volume sub-sources. The initial prior data may be used as input into computing device 303 or another computing device (e.g., computing device 101, imaging device 301, etc.) for additional processing 340 (e.g., conventional reconstruction techniques of luminescence images).

Figure 4:
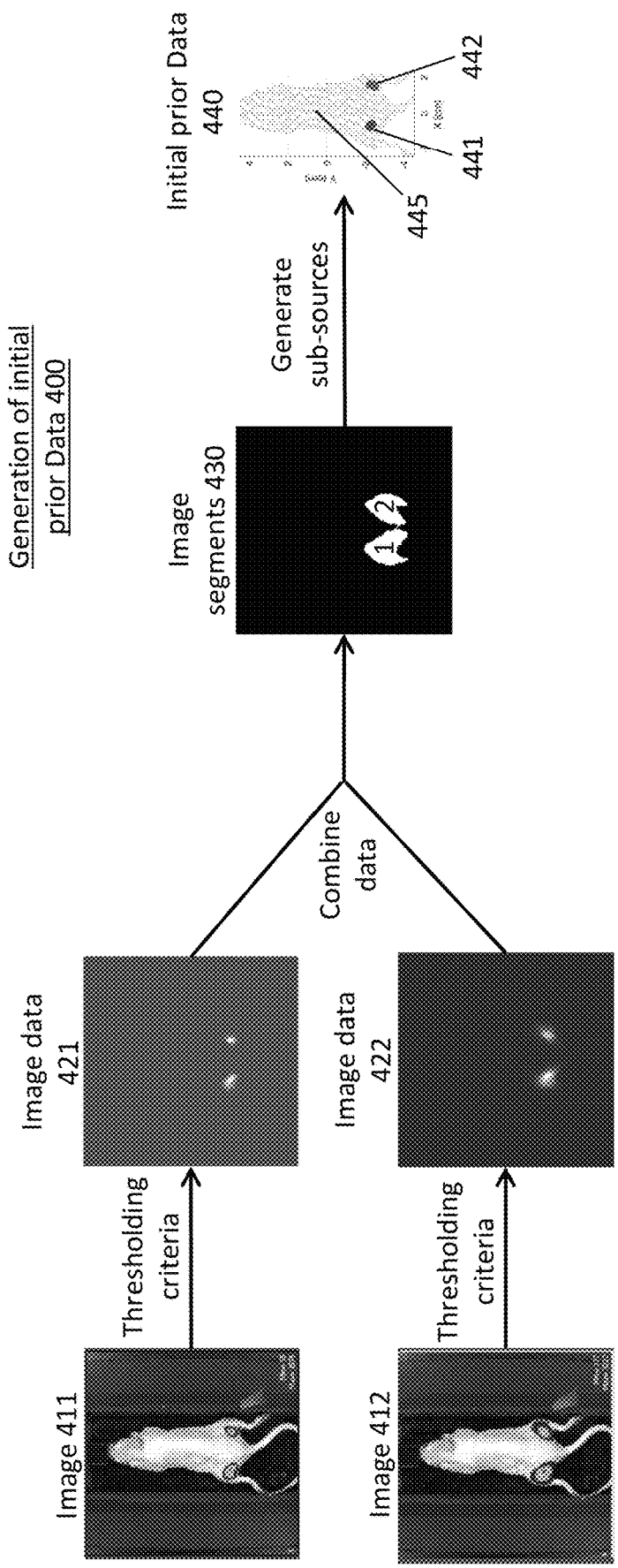
FIG. 4 shows an example process for generating initial prior data.

FIG. 4 shows an example process 400 for generating initial prior data. For example, thresholding criteria (further discussed below in connection with FIG. 5B) may be applied to the luminescence image pair (e.g., images 411 and 412). Image data (e.g., image data 421 and 422), generated based on applying thresholding criteria, may be combined into a single image dataset. The single image dataset may be further processed and segmented into one or more image segments 430 (see the discussion below in connection with FIG. 5B). The image segments may be further processed to generate one or more volume sub-regions 441 and 442 as reconstructed sources located within the scattering medium. Surface data 445, e.g., received from the additional information in step 201, may indicate a surface boundary of the scattering medium. The output initial prior data 440 may comprise one or more volume sub-regions 441 and 442 and the surface data 445. An example method for implementing the example process depicted in FIG. 4 is discussed below in connection with FIGS. 5A-5C.

Figure 5A:
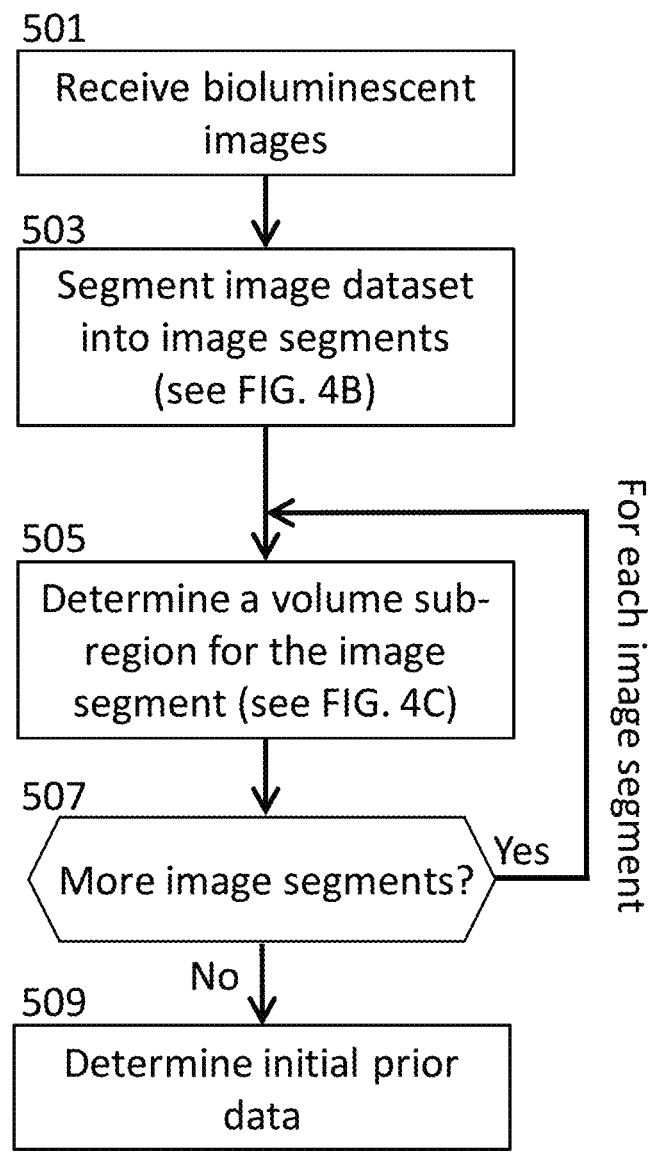
FIGS. 5A, 5B, and 5C are a flowchart showing an example method of determining initial prior data.
Figure 5B:
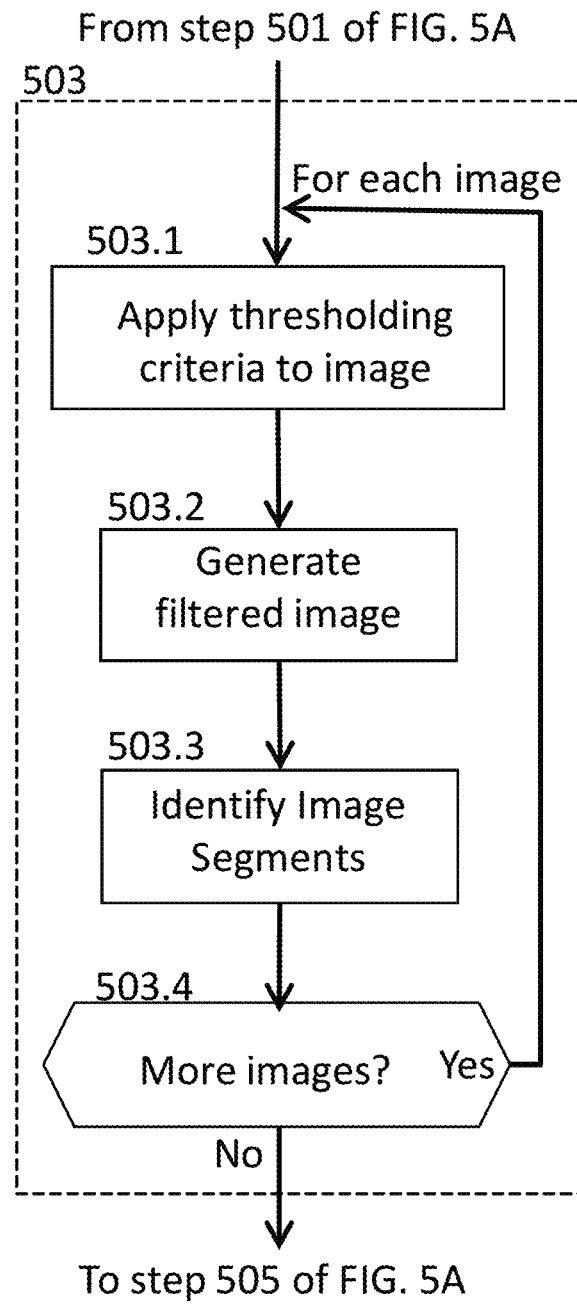
Figure 5C:
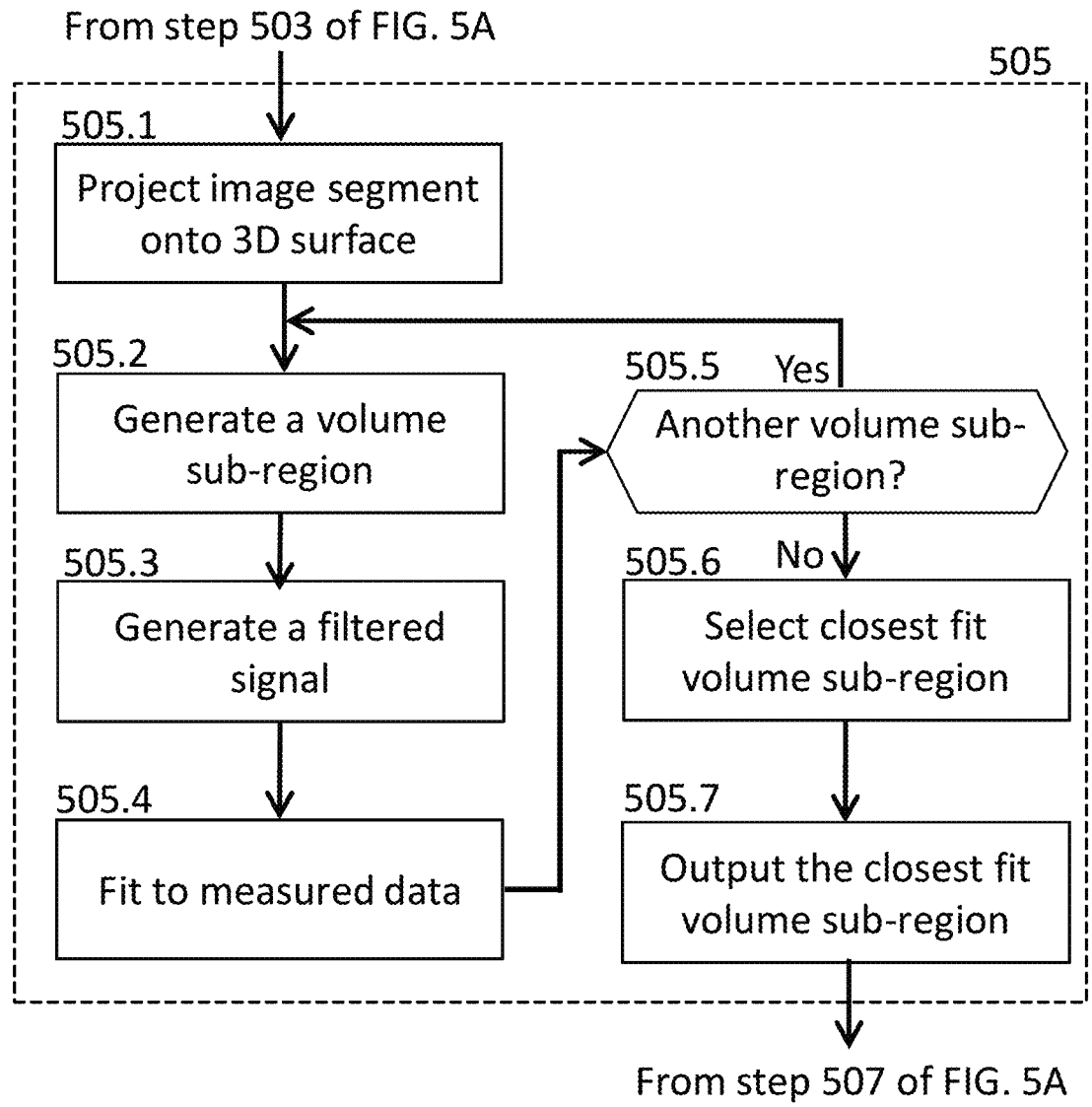

FIGS. 5A-5C are a flowchart showing an example method of determining initial prior data. One, some, or all steps of the example method of FIGS. 5A-5C may be performed by one or more computing devices, and for convenience FIGS. 5A-5C will be described below in connection with the computing device 303. Also or alternatively, one, some, or all steps of the example method of FIGS. 5A-5C may be performed by one or more other computing devices (e.g., computing device 101, computing device 303, imaging device 301, etc.). One or more steps of the example method of FIGS. 5A-5C may be rearranged (e.g., performed, sent, or received in a different order), omitted, and/or otherwise modified, and/or other steps and/or communications added.

In step 501, computing device 303 may receive luminescence images from the imaging device 301. For example, the luminescence images may comprise a first luminescence image based on a first optical filter (e.g., one of two optical filters of an optical filter pair) and a second luminescence image based on a second optical filter (e.g., another of the two optical filters of the optical filter pair). The luminescence images may have been generated based on the luminescence imaging process discussed above in connection with FIG. 3. Furthermore, the first optical filter and the second optical filter may have been selected based on the optical filter pair selection process discussed above in connection with FIG. 1 and FIGS. 2A-2C.

In step 503, one or more image segments may be generated for the luminescence images. For example, an image dataset may be generated based on a performing one or more of a sum, an average, or a weighted sum of the luminescence images. The computing device 303 may determine that one or more portions of the image dataset may be segmented into one or more image segments. A boundary of an image segment may comprise any geometric and/or polygonal shape associated with the luminescence image. The one or more image segments may be contiguous or non-contiguous. Also or alternatively, one or more of the one or more image segments may fully or partially overlap with each other. Also or alternatively, the one or more image segments may correspond to portions of a 3D surface associated with the luminescence images. One or more image segments may be determined for each of the luminescence images of the luminescence image pair. Additional details of step 403 are described below in connection with FIG. 5B.

In step 505, one or more volume sub-regions may be generated based on the one or more image segments determined in step 503. A volume sub-region may comprise one or more voxels. Each of the voxels of a volume sub-region may be assigned a radiation value based on the luminescent source and one or more optical filters (e.g., an optical filter pair). The one or more volume sub-regions may be contiguous or non-contiguous with respect to each other. Also or alternatively, a volume sub-region may fully or partially overlap with one or more other volume sub-regions. Additional details of step 505 are described below in connection with FIG. 5C.

In step 507, the computing device 303 may determine whether there are additional image segments to process. Additional image segments may be associated with either of the two luminescence images of the pair of luminescence images. If the computing device 303 determines that there are additional segments to process, step 505 may be performed. Otherwise step 509 may be performed.

In step 509, initial prior data may be generated based on the one or more volume sub-regions. The initial prior data may comprise a reconstruction of the luminescent source. The reconstruction of the luminescent source may comprise a volume region comprising a plurality of voxels. Each of the plurality of voxels may be assigned one or more radiation values (e.g., intensity or electric field). For example, the reconstructed luminescent source may be generated based on performing an average of the radiation values, over each voxel, for the one or more volume sub-regions. Also or alternatively, the reconstructed luminescent source may be generated based on adding, for each voxel, the radiation values of the one or more volume sub-regions. Also or alternatively, the reconstructed luminescent source may be generated based on performing, for each voxel, a weighted sum of the radiation values of the one or more volume sub-regions.

FIG. 5B shows, as indicated by a broken line box, additional details of step 503 from FIG. 5A. In particular, FIG. 5B shows examples steps 503.1-503.4 that may be performed to generate one or more image segments from a luminescence image. In step 503.1, a luminescence image (e.g., one of the received luminescence images of step 501) may be selected. One or more thresholding criteria may be applied to the luminescence image. For example, applying the one or more thresholding criteria may comprise determining numerical values associated with each pixel of the luminescence image. Image segments may be generated based on pixels comprising numerical values above a threshold value. Also or alternatively, the criteria may comprise fitting a Gaussian function to a histogram of numerical values associated with each pixel of the luminescence image. Numerical values above a threshold value of the Gaussian function (e.g., above the center of the Gaussian plus full-width-half-maximum) may be associated with an image segment, and numerical values below the threshold value may be associated with a background. A mixed Gaussian model may also be used.

In step 503.2, a filtered image may be generated based on the applied one or more thresholding criteria of step 503.1. For example, a filtered image comprising background and image segment pixels may be generated. A pixel of the filtered image may map to a sibling pixel of the luminescence image. Thus, pixels of the filtered image may be assigned a background numerical value (e.g., 0) if the sibling pixel of the luminescence image failed one or more of the thresholding criteria. Moreover, pixels of the filtered image may be assigned an image segment numerical value (e.g., 255) if the sibling pixel of the luminescence image passed one or more of the thresholding criteria. Also or alternatively, the background and image segment pixels of the filtered image may comprise any other two numerical values that may be used to distinguish between pixels associated with image segments and pixels associated with background.

In step 503.3, one or more image segments may be generated from the filtered image. For example, the computing device 303 may determine that one or more image segment pixels of the filtered image are enclosable within a single closed polygon or other geometric shape. The closed polygon or other geometric shape may indicate a boundary region of an image segment. Also or alternatively, the computing device 303 may determine that a portion of the one or more image segment pixels of the filtered image may be enclosed in a first closed polygonal shape and a second portion of the one or more image segment pixels of the filtered image may be enclosed in a second closed polygonal shape. The first and second closed polygonal shapes may correspond to boundary regions of first and second image segments. Also or alternatively, the computing device 303 may determine that a plurality of portions of the one or more image segment pixels of the filtered image may be enclosed in a plurality of closed polygonal shapes. The plurality of closed polygonal shapes may correspond to boundary regions of a plurality of image segments.

In step 503.4, the computing device 303 may determine whether additional luminescence images are available for image segmentation. If additional luminescence images are available for image segmentation, step 503.1 may be performed. Otherwise step 505 of FIG. 5A may be performed.

FIG. 5C shows, as indicated by a broken line box, additional details of step 505 from FIG. 5A. In particular, FIG. 5C shows examples steps 505.1-505.7 that may be performed to generate a luminescent sub-source based on an image segment. In step 505.1, an image segment may be projected, by the computing device 303, onto the surface boundary of the scattering medium. For example, the scattering medium may comprise a plurality of voxels. A portion of the plurality of voxels may comprise surface voxels corresponding to the surface boundary of the scattering medium. The computing device 303 may associate one or more of the surface voxels with an image segment.

In step 505.2, a volume sub-region may be generated. For example, the volume sub-region may comprise one or more voxels. The one or more voxels may be contiguous or non-contiguous. Furthermore, a location for each of the one or more voxels may be generated, by the computing device 303, using a pseudo-random generator, and the volume sub-region may correspond to a pseudo-randomly generated 3D shape. Alternatively, the one or more voxels may be generated based on one or more pre-determined volume sub-region shapes (e.g., a spherical or ellipsoidal region of space). For example, a volume sub-region may be ellipsoidal in shape based on being located within a predetermined surface distance of a surface boundary of the scattering medium. Alternatively, the volume sub-region may be spherical based on being located outside of the predetermined surface distance from the surface boundary. Also or alternatively, the volume sub-region may be ellipsoidal in shape independent of its surface distance from the surface boundary of the scattering medium. Also or alternatively, a volume sub-region may be spherical in shape independent of its surface distance from the surface boundary of the scattering medium.

Moreover, each of the one or more voxels of a volume sub-region may be assigned a radiation value (e.g., radiated intensity or radiated electric field strength) for one or more spectral values (e.g., 560 nm and 620 nm, or any other optical wavelengths associated with one or more optical filters). Also or alternatively, each of the one or more voxels of the volume sub-region may be assigned a radiation type (e.g., electric monopole, electric dipole, directional planewave, cylindrical wave, spherical wave, etc.).

In step 505.3, a filtered signal may be generated based on the assigned radiation values of the one or more voxels of the volume sub-region. For example, the computing device 303 may simulate the transmission of electromagnetic radiation based on the radiation values assigned to each of the voxels of the volume region. The one or more voxels may be configured to radiate as electric monopoles. Also or alternatively, the one or more voxels may be configured to radiate as electric dipoles. Also or alternatively, radiation emitted from a voxel may be a plane wave, a spherical wave, a cylindrical wave, or any other type of electromagnetic wave. The filtered signal may comprise a composite sum of electric fields emitted by each of the one or more voxels. Alternatively, the filtered signal may comprise a composite sum of radiated intensity emitted by each of the one or more voxels. The filtered signal may be scattered and/or absorbed by the scattering medium and thus may be attenuated as it propagates through the scattering medium. Upon exiting the scattering medium, the computing device 303 may apply an optical filter (e.g., one of the optical filters of an optimal filter pair) to the optical signal. For example, one or more of the spectral components of the optical signal may be altered based on applying the optical filter.

In step 505.4, the filtered signal may be compared with measured data (e.g., the luminescence images or the image dataset). For example, the computing device may generate a reconstruction of the image dataset ("reconstructed image") based on the filtered signal. For a given spectral component, a correlation may be determined between the reconstructed image and the image dataset. For example, a root-mean-square deviation may be determined between the reconstructed image and the image dataset. A root-mean-square deviation value that falls below a pre-determined deviation threshold value may correspond to a high correlation between the reconstructed image and the image dataset. An output correlation between the filtered signal and the measured data may be determined based on the determined correlations between the reconstructed image and the image dataset. For example, the output correlation may be determined based on at least one or more of averaging the correlations, summing the correlations, taking a product of the correlations, or performing a weighted sum of the correlations.

In step 505.5, the computing device 303 may determine whether to generate another volume sub-region. For example, the computing device 303 may generate a pre-determined number of volume sub-regions (e.g., generate volume sub-regions for a pre-determined number of distances below the surface of the scattering medium). Also or alternatively, the computing device 303 may continue generating volume sub-regions until no further improvements in the signal fit of step 505.4 are detectable. If the computing device 303 determines that another volume sub-regions should be generated, step 505.2 may be performed. Otherwise step 505.6 may be performed.

In step 505.6, a closest fit volume sub-region may be selected. For example, the computing device 303 may select a volume sub-region associated with a highest valued output correlation (e.g., computed in step 505.4). In step 505.7, the selected volume sub-region may be sent to a memory or storage device associated with the computing device 303.

Some embodiments may include one or more non-transitory computer-readable media (e.g., computer-readable media 105 or 307) that store instructions that, when executed by a processor (e.g., processors 103 or 305) of a computing device (e.g., the imaging device 301, computing device 101, or computing device 303) perform the methods described here.

In the above description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope of the present disclosure. Aspects of the disclosure are capable of other embodiments and of being practiced or being carried out in various ways. In addition, it is to be understood that the phraseology and terminology used herein are for the purpose of description and should not be regarded as limiting. Rather, the phrases and terms used herein are to be given their broadest interpretation and meaning.

Use of ordinal terms such as "first," "second," "third," etc., in the claims to modify a claim element does not by itself connote any priority, precedence, or order of one claim element over another, but are used merely as labels to distinguish one claim element having a certain name from another element having a same name (but for use of the ordinal term) to distinguish the claim elements.

The indefinite articles "a" and "an," as used herein in the specification and in the claims, unless clearly indicated to the contrary, should be understood to mean "at least one."

The phrase "and/or" as used herein in the specification and in the claims, should be understood to mean "either or both" of the elements so conjoined, i.e., elements that are conjunctively present in some cases and disjunctively present in other cases.

Although examples are described above, features and/or steps of those examples may be combined, divided, omitted, rearranged, revised, and/or augmented in any desired manner. Various alterations, modifications, and improvements will readily occur to those skilled in the art. Such alterations, modifications, and improvements are intended to be part of this description, though not expressly stated herein, and are intended to be within the spirit and scope of the disclosure. Accordingly, the foregoing description is by way of example only, and is not limiting.

The invention claimed is:
1. A method comprising:
receiving, from a user device, one or more images, wherein each image, of the one or more images, was generated by application of a corresponding optical filter, of one or more optical filters, to light from a bioluminescent source located within a volume of biological material;

determining, based on the one or more images, one or more image segments;

generating one or more volume sub-regions by, for each volume sub-region, of the one or more volume sub-region, corresponding to an image segment of the one or more image segments:
- generating one or more volume test-regions, wherein each of the one or more volume test-regions comprise one or more voxels assigned one or more radiation test-values, and wherein the one or more radiation test-values are determined based on the bioluminescent source, the volume of biological material, and the one or more optical filters;
- generating, based on the one or more radiation test-values assigned to the one or more voxels and the one or more optical filters, one or more test images;
- generating, based on the one or more test images, image test-segments;
- determining correlation values between the image test-segments and the image segment; and
- selecting, based on the correlation values of the image test-segments, a volume test-region as the volume sub-region;

determining, based on the one or more volume sub-regions, an output volume region comprising output voxels, wherein one or more output radiation values are assigned to each of the output voxels; and causing image reconstruction, by a computing device and based on the output volume region, of the bioluminescent source.

2. The method of claim 1, wherein the determining the one or more image segments comprises comparing numerical values of pixels of the one or more images with one or more threshold values.

3. The method of claim 1, wherein a quantity of the one or more image segments is less than a pre-determined quantity of image segments.

4. The method of claim 1, further comprising sending, to a storage device, the output volume region.

5. The method of claim 1, further comprising:
determining, for a volume sub-region, a distance between a voxel associated with the volume sub-region and a surface boundary of the volume of biological material.

6. The method of claim 1, wherein the output volume region is determined based on performing an average, for one or more voxels of the one or more volume sub-regions, of the radiation values assigned to the one or more voxels.

7. The method of claim 1, wherein the user device corresponds to a three-dimensional bioluminescent imaging device.

8. The method of claim 1, wherein
the selecting the volume test-region as the volume sub-region is based on determining a highest correlation value, of the correlation values, corresponding to an image test-segment, of the image test-segments, corresponding to the volume test-.

9. The method of claim 1, wherein the one or more optical filters comprise a first optical filter and a second optical filter, and wherein the first and second optical filters correspond to an optical filter pair selected from a list of available optical filters.

10. The method of claim 1, further comprising:
receiving, from a user device, one or more additional images associated with one or more additional optical filters and the bioluminescent source located within the volume of biological material;
determining, based on the one or more additional images, one or more additional image segments;
generating one or more additional volume sub-regions associated with the one or more additional image segments, wherein each of the one or more additional volume sub-regions comprises additional voxels, and wherein each of the additional voxels is assigned one or more additional radiation values determined based on the bioluminescent source, the volume of biological material, and the one or more additional optical filters;
determining, based on the one or more additional volume sub-regions, a second output volume region comprising additional output voxels, wherein one or more output radiation values are assigned to each of the additional output voxels; and
sending, to the computing device and for additional processing, the second output volume region.

11. One or more non-transitory computer-readable media storing instructions that, when executed, cause:
receiving, from a user device, one or more images, wherein each image, of the one or more images, was generated by application of a corresponding optical filter, of one or more optical filters, to light from a bioluminescent source located within a volume of biological material;
determining, based on the one or more images, one or more image segments;
generating one or more volume sub-regions by, for each volume sub-region, of the one or more volume sub-region, corresponding to an image segment of the one or more image segments:
- generating one or more volume test-regions, wherein each of the one or more volume test-regions comprise one or more voxels assigned one or more radiation test-values, and wherein the one or more radiation test-values are determined based on the bioluminescent source, the volume of biological material, and the one or more optical filters;
- generating, based on the one or more radiation test-values assigned to the one or more voxels and the one or more optical filters, one or more test images;
- generating, based on the one or more test images, image test-segments;
- determining correlation values between the image test-segments and the image segment; and
- selecting, based on the correlation values of the image test-segments, a volume test-region as the volume sub-region;
determining, based on the one or more volume sub-regions, an output volume region comprising output voxels, wherein one or more output radiation values are assigned to each of the output voxels; and
causing image reconstruction, by a computing device and based on the output volume region, of the bioluminescent source.

12. The one or more non-transitory computer-readable media of claim 11, wherein the determining the one or more image segments comprises comparing numerical values of pixels of the one or more images with one or more threshold values.

13. The one or more non-transitory computer-readable media of claim 11, wherein the output volume region is determined based on performing an average, for one or more voxels of the one or more volume sub-regions, of the radiation values assigned to the one or more voxels.

14. The one or more non-transitory computer-readable media of claim 11, wherein the user device corresponds to a three-dimensional bioluminescent imaging device.

15. The one or more non-transitory computer-readable media of claim 11, wherein the selecting the volume test-region as the volume sub-region is based on determining a highest correlation value, of the correlation values, corresponding to an image test-segment, of the image test-segments, corresponding to the volume test-region.

16. The one or more non-transitory computer-readable media of claim 11, wherein a quantity of the one or more image segments is less than a pre-determined quantity of image segments.

17. A system comprising:
a user device;
a computing device comprising:
 one or more processors; and
 memory storing instructions that, when executed by the one or more processors, cause the computing device to:
  receive, from the user device, one or more images, wherein each image, of the one or more images, was generated by application of a corresponding optical filter, of one or more optical filters, to light from a bioluminescent source located within a volume of biological material;
  determine, based on the one or more images, one or more image segments;
  generate one or more volume sub-regions by, for each volume sub-region, of the one or more volume sub-region, corresponding to an image segment of the one or more image segments;
   generating one or more volume test-regions, wherein each of the one or more volume test-regions comprise one or more voxels assigned one or more radiation test-values, and wherein the one or more radiation test-values are determined based on the bioluminescent source, the volume of biological material, and the one or more optical filters;
   generating, based on the one or more radiation test-values assigned to the one or more voxels and the one or more optical filters, one or more test images;
   generating, based on the one or more test images, image test-segments;
   determining correlation values between the image test-segments and the image segment; and
   selecting, based on the correlation values of the image test-segments, a volume test-region as the volume sub-region;
  determine, based on the one or more volume sub-regions, an output volume region comprising output voxels, wherein one or more output radiation values are assigned to each of the output voxels; and
  cause image reconstruction, based on the output volume region, of the bioluminescent source.

18. The system of claim 17, wherein the user device corresponds to a three-dimensional bioluminescent imaging device.

19. The system of claim 17, wherein the output volume region is determined based on performing an average, for one or more voxels of the one or more volume sub-regions, of the radiation values assigned to the one or more voxels.

20. The system of claim 17, wherein the determining the one or more image segments of comprises comparing numerical values of pixels of the one or more images with one or more threshold values.

\* \* \* \* \*